US011462312B1

(12) United States Patent
Rogers et al.

(10) Patent No.: US 11,462,312 B1
(45) Date of Patent: Oct. 4, 2022

(54) MEDICATION INVENTORY SYSTEM INCLUDING MOBILE DEVICE BASED MISSING MEDICATION DETERMINATION AND RELATED METHODS

(71) Applicant: INMAR Rx SOLUTIONS, INC., Ft. Worth, TX (US)

(72) Inventors: Brian S. Rogers, Greensboro, NC (US); James W. McCracken, Jr., Lewisville, NC (US); Seth Maxwell, Lewisville, NC (US); Michael A. Snellenburg, Winston-Salem, NC (US); Marko Milojevic, Jamestown, NC (US); Patrick S. Connelly, Carnegie, PA (US); Justin A. Krull, Hurst, TX (US); Jared O. Santibanez, Forney, TX (US); Greg J. Brendel, West Mifflin, PA (US)

(73) Assignee: INMAR RX SOLUTIONS, INC., Ft. Worth, TX (US)

( * ) Notice: Subject to any disclaimer, the term of this patent is extended or adjusted under 35 U.S.C. 154(b) by 400 days.

(21) Appl. No.: 16/704,573

(22) Filed: Dec. 5, 2019

(51) Int. Cl.
*G16H 20/10* (2018.01)
*A61J 7/04* (2006.01)
(Continued)

(52) U.S. Cl.
CPC ............... *G16H 20/10* (2018.01); *A61J 1/03* (2013.01); *A61J 7/0069* (2013.01); *A61J 7/0084* (2013.01);
(Continued)

(58) Field of Classification Search
CPC ....... G16H 20/10; G16H 30/00; A61J 7/0409; A61J 7/0069; A61J 7/0084; A61J 1/03;
(Continued)

(56) References Cited

U.S. PATENT DOCUMENTS 3,069,654 A 12/1962 Hough
4,768,661 A 9/1988 Pfeifer
(Continued)

OTHER PUBLICATIONS

McCracken, Jr. et al., U.S. Appl. No. 16/395,343, filed Apr. 26, 2019.
(Continued)

*Primary Examiner* — Michael Collins
(74) *Attorney, Agent, or Firm* — Allen, Dyer, Doppelt + Gilchrist, P.A.

(57) ABSTRACT

A medication inventory system may include a medication tray that includes compartments for storing respective medications with each medication having a respective medication identifier associated therewith. The medication tray may have a tray identifier associated therewith. The medication inventory system may also include a mobile wireless communications device configured to obtain images of the medication tray and generate a current medication stocking list of the medication tray from the images. The medication inventory system may also be configured to determine a desired medication stocking list for the medication tray based upon the tray identifier and determine at least one missing medication based upon the current medication stocking list and the desired medication stocking list.

27 Claims, 11 Drawing Sheets

(51) Int. Cl.
    *A61J 7/00*         (2006.01)
    *G16H 30/00*     (2018.01)
    *A61J 1/03*         (2006.01)
    *G06Q 10/08*     (2012.01)

(52) U.S. Cl.
    CPC .......... *A61J 7/0409* (2013.01); *G06Q 10/087* (2013.01); *G16H 30/00* (2018.01); *A61J 2205/10* (2013.01); *A61J 2205/60* (2013.01)

(58) Field of Classification Search
    CPC .. A61J 2205/60; A61J 2205/10; G06Q 10/087
    See application file for complete search history.

(56) References Cited

U.S. PATENT DOCUMENTS

| | | | |
|---|---|---|---|
| 7,085,432 B2 | 8/2006 | Paquette | |
| 7,599,516 B2 * | 10/2009 | Limer | G06V 20/66 |
| | | | 453/4 |
| 8,861,816 B2 * | 10/2014 | Lang | G06K 9/6293 |
| | | | 382/128 |
| 8,966,863 B2 | 3/2015 | Amano et al. | |
| 9,757,305 B2 * | 9/2017 | Ika | A61J 7/0069 |
| 10,083,366 B2 | 9/2018 | Song et al. | |
| 10,357,428 B2 * | 7/2019 | Ika | A61J 1/03 |
| 11,030,752 B1 | 6/2021 | Backlund et al. | |
| 2007/0239482 A1 | 10/2007 | Finn et al. | |
| 2010/0027845 A1 | 2/2010 | Kim et al. | |
| 2013/0070090 A1 * | 3/2013 | Bufalini | G16H 20/13 |
| | | | 348/143 |
| 2013/0091679 A1 * | 4/2013 | Gloger | G16H 40/63 |
| | | | 29/407.04 |
| 2014/0214438 A1 | 7/2014 | Ahmadi | |
| 2014/0288952 A1 * | 9/2014 | Smith | G06Q 40/08 |
| | | | 705/2 |
| 2016/0147976 A1 * | 5/2016 | Jain | G16H 20/10 |
| | | | 705/2 |
| 2016/0364686 A1 | 12/2016 | Wolfe et al. | |
| 2017/0098049 A1 * | 4/2017 | Sweeney | A61B 90/361 |
| 2017/0246083 A1 | 8/2017 | Amano et al. | |
| 2017/0270508 A1 | 9/2017 | Roach et al. | |
| 2018/0260665 A1 | 9/2018 | Zhang et al. | |
| 2019/0333008 A1 | 10/2019 | Wolfe et al. | |
| 2020/0296062 A1 * | 9/2020 | Wilson | H04L 51/10 |
| 2021/0298994 A1 | 9/2021 | Liu et al. | |
| 2022/0008291 A1 * | 1/2022 | Grosfils | B65B 57/18 |

OTHER PUBLICATIONS

McCracken, Jr. et al., U.S. Appl. No. 16/395,353, filed Apr. 26, 2019.

* cited by examiner

MEDICATION INVENTORY SYSTEM INCLUDING MOBILE DEVICE BASED MISSING MEDICATION DETERMINATION AND RELATED METHODS

TECHNICAL FIELD

The present invention relates to the field of medicine, and more particularly, to medication inventory systems and related methods.

BACKGROUND

Medications, including controlled substances, medical devices, and/or medical tools may be relatively important for treatment of a patient. Thus, it may be desirable to maintain medications in a relatively orderly and predictable fashion to reduce the amount of time it takes to access these medications, particularly in a time sensitive situation.

A medication tray is often used to provide a specific selection and quantity of medications for a particular medical use case, physician preference, and/or location. A given health care facility may have multiple variations of medication trays in use, each varying in type, amount, and/or placement of medications within the medication tray. Multiple medication trays may be used within a crash cart, which is a wheeled cart for dispensing of medication (e.g., in an emergency). Consequently, health care facility pharmacies may process and manage a relatively large quantity of medication trays used throughout a facility.

Accordingly, the medication trays are typically managed. Contents of the medication trays may be replenished and verified, for example, between uses. The verification may be performed manually and include inspection for recalled, expired, and misplaced medications.

U.S. Patent Application Publication No. 2017/0246083 to Amano et al. is directed to a medicine sorting apparatus. More particularly, Amano et al. discloses a medicine sorting apparatus that includes an identifying part, e.g., based upon a camera, which can identify a direction, a posture and characteristics such as a shape, a size, a type and an expiration date of a medicine, and a storing part for storing the medicine so that the medicine can be taken from the storing part. A determination processing part can determine whether or not the medicine is a target to be treated based on the characteristics of the medicine identified by the identifying part.

U.S. Patent Application Publication No. 2018/0260665 to Zhang et al. is directed to a deep learning system for recognizing pills in images. More particularly, the system and method use deep learning, including convolutional neural networks, to identify subject objects in unconstrained user images such as unknown pills. An image of, e.g., a pill, may be captured and subsequently processed using deep learning models to identify the pill. The deep learning models may be optimized to have a small footprint (in terms of computational and memory resources) suitable for a resource-limited device such as a smartphone while retaining a high object recognition accuracy. Each such model may also be run on modified versions of the unconstrained image, for example on color, greyscale, and gradient images, to focus the models on different distinguishing features of the object.

SUMMARY

A medication inventory system may include a medication tray that may include a plurality of compartments for storing respective medications with each medication having a respective medication identifier associated therewith. The medication tray may have a tray identifier associated therewith. The medication inventory system may also include a mobile wireless communications device configured to obtain a plurality of images of the medication tray and generate a current medication stocking list of the medication tray from the plurality of images. The medication inventory system may also be configured to determine a desired medication stocking list for the medication tray based upon the tray identifier and determine at least one missing medication based upon the current medication stocking list and the desired medication stocking list.

The mobile wireless communications device may be configured to generate the current medication stocking list of the medication tray based upon combining the plurality of images, for example. The mobile wireless communications device may be configured to generate the current medication stocking list of the medication tray based upon a homographic algorithm applied to the plurality of images.

The mobile wireless communications device may be configured to generate the current medication stocking list of the medication tray based upon a homographic algorithm applied to the plurality of images based upon respective locations of the medication identifiers, for example. The mobile wireless communications device may be configured to determine expired medications within the medication tray based upon the medication identifiers, and generate and communicate an expiration notification based thereon.

The mobile wireless communications device may be configured to determine medications within the medication tray within a threshold time from expiration based upon the medication identifiers, and generate and communicate an expiration notification based thereon, for example. The plurality of images may include a plurality of images having different fields of view relative to the medication tray, for example.

The mobile wireless communications device may be configured to determine current medication locations within the medication tray from the plurality of images and determine desired medication locations for the tray based upon the tray identifier. The mobile wireless communications device may also be configured to determine at least one misplaced medication based upon the current medication locations and the desired medication locations, for example.

The mobile wireless communications device may be configured to communicate the plurality of images to a remote computer for storage thereon. The mobile wireless communications device may include a housing and wireless communications circuitry carried by the housing, for example.

The medication identifiers may include barcodes. The medication identifiers may include quick-response (QR) codes, for example.

A method aspect is directed to a method of processing medication inventory in a medication inventory system that includes a medication tray including a plurality of compartments for storing respective medications with each medication having a respective medication identifier associated therewith. The medication tray may have a tray identifier associated therewith. The method may include using a mobile wireless communications device to obtain a plurality of images of the medication tray and generate a current medication stocking list of the medication tray from the plurality of images. The method may also include using the mobile wireless communications device to determine a desired medication stocking list for the medication tray based upon the tray identifier and determine at least one missing medication based upon the current medication stocking list and the desired medication stocking list.

A computer readable medium aspect is directed to a non-transitory computer readable medium for a medication inventory system that includes a medication tray including a plurality of compartments for storing respective medications with each medication having a respective medication identifier associated therewith. The medication tray may have a tray identifier associated therewith, the non-transitory computer readable medium includes computer executable instructions that when executed by a controller of a mobile wireless communications device cause the controller to perform operations. The operations may include obtaining a plurality of images of the medication tray and generating a current medication stocking list of the medication tray from the plurality of images. The operations may also include determining a desired medication stocking list for the medication tray based upon the tray identifier, and determining at least one missing medication based upon the current medication stocking list and the desired medication stocking list.

DETAILED DESCRIPTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and prime notation is used to indicate similar elements in alternative embodiments.

Figure 1:
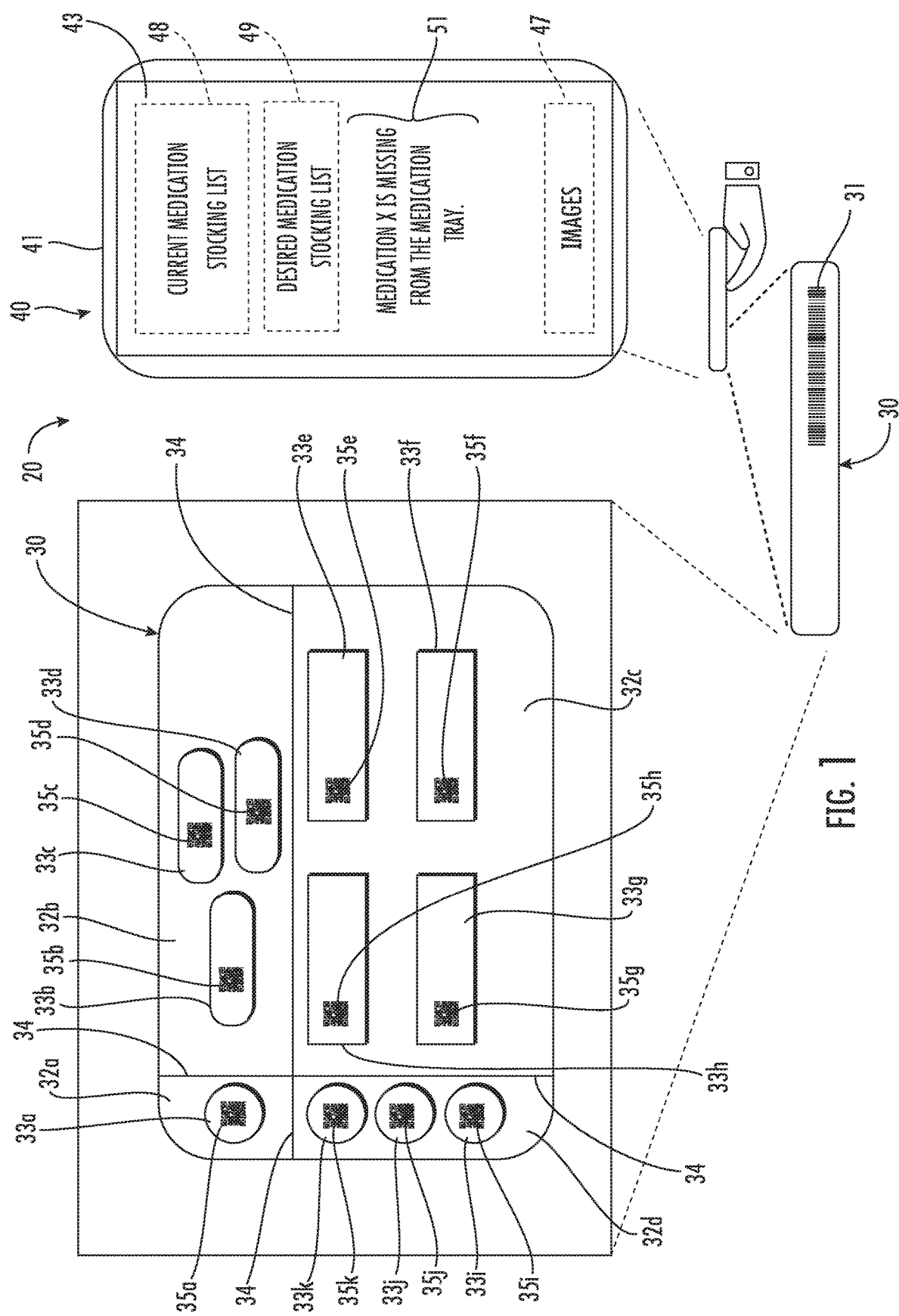
FIG. 1 is a schematic diagram of a medication inventory system in accordance with an embodiment.
Figure 2:
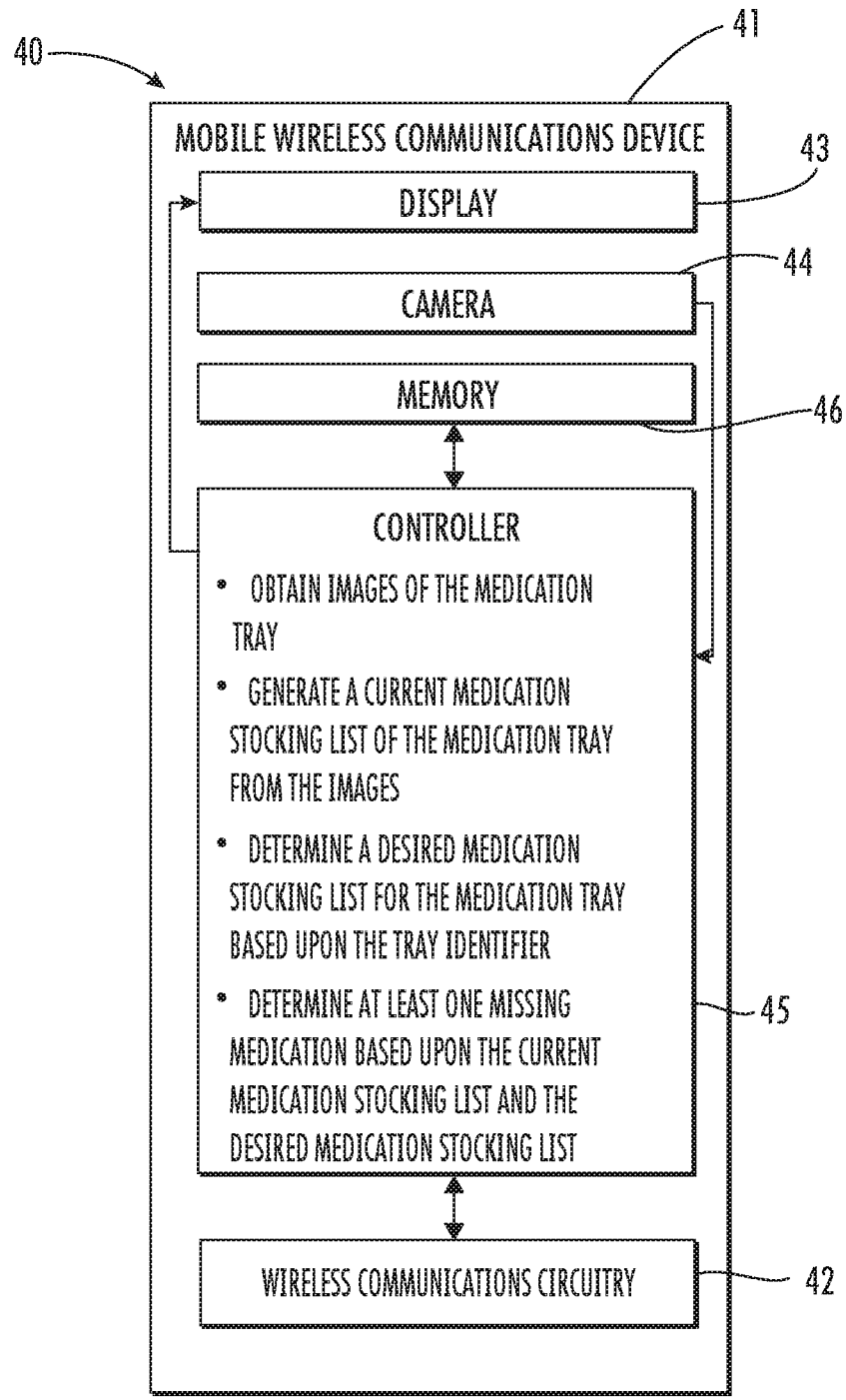
FIG. 2 is a schematic block diagram of the medication inventory system of FIG. 1.

Referring initially to FIGS. 1 and 2, a medication inventory system 20 illustratively includes a medication tray 30. The medication tray 30 includes partitions 34 that define compartments 32a-32n. Each compartment may store a medication 33a-33n, multiple medications, a medical or medicated device, a medication container that includes individual medications therein, or other item or substance used for medical treatment. For example, the medication tray 30 may be part of a crash cart, as will be appreciated by those skilled in the art. Of course, the medication tray 30 may be used in other medical environments, for example, an examination room, emergency room, treatment room, operating room, etc. For example, the medication tray 30 may be in the form of a drawer within a medication cabinet or medication dispensing cabinet. Each medication 33a-33n has a respective medication identifier 35a-35n associated therewith, for example, a barcode, quick-response (QR) code, alphanumeric characters, or other optically recognizable and unique code.

The medication tray 30 has a tray identifier 31 associated therewith. The tray identifier 31 may be in the form of a barcode, for example, that may be printed or applied (e.g., via an adhesive label) on the medication tray 30. The tray identifier 31 may be in the form of another type of identifier, for example, QR code, alphanumeric characters, or other optically recognizable and unique code.

The medication inventory system 20 also includes a mobile wireless communications device 40, illustratively in the form of a smartphone. The mobile wireless communications device 40 illustratively includes a housing 41 and wireless communications circuitry 42 carried by the housing. The mobile wireless communications device 40 also includes a display 43, for example, a touch display, carried by the housing 41. A controller 45 is coupled to the wireless communications circuitry 42 and the display 43. A camera 44 is also carried by the housing 41 and coupled to the controller 45. One or more input devices may be carried by the housing 41 and coupled to the controller 45. While the mobile wireless communications device 40 is illustratively in the form of a smartphone, the mobile wireless communications device may be in the form of a tablet, laptop computer, or wearable device, for example.

Figure 3:
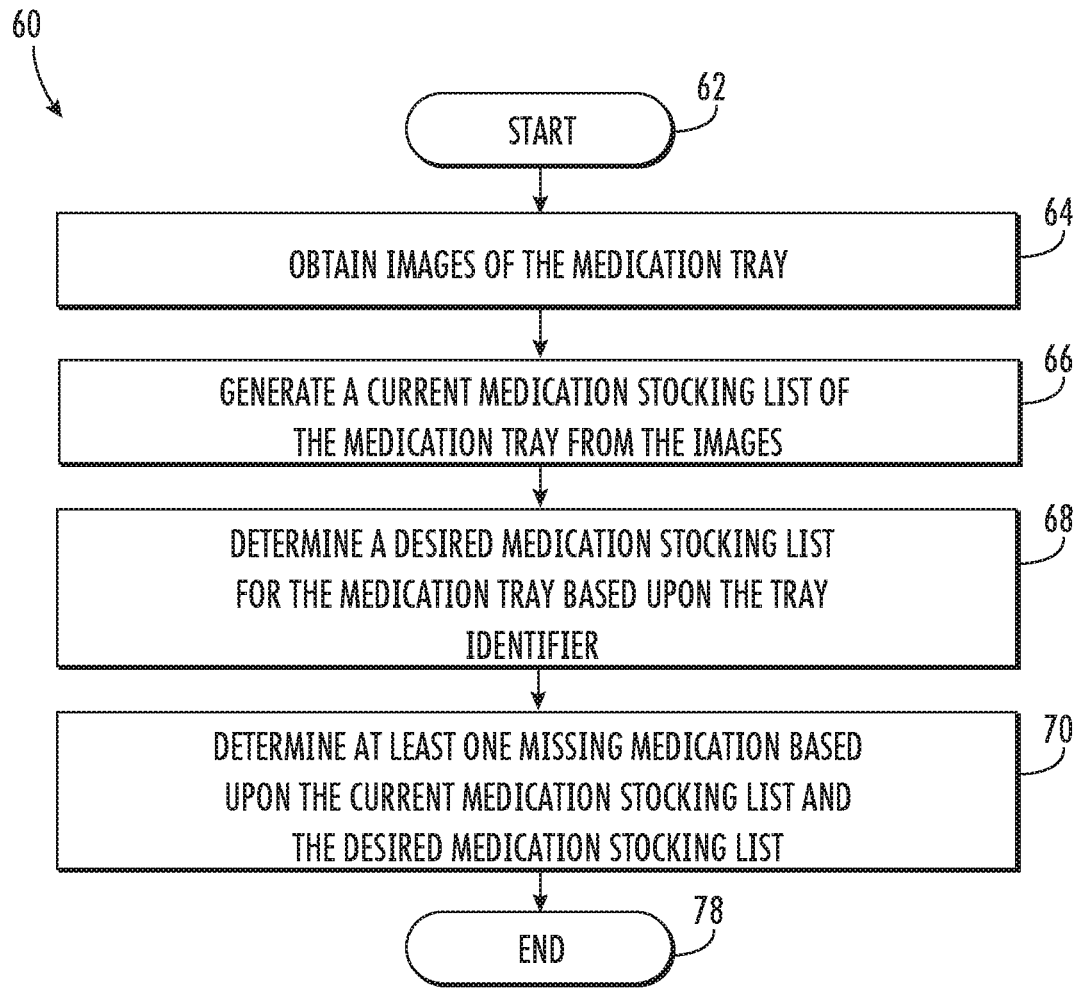
FIG. 3 is a flow diagram illustrating operation of the mobile wireless communications device of FIG. 2.
Figure 4:
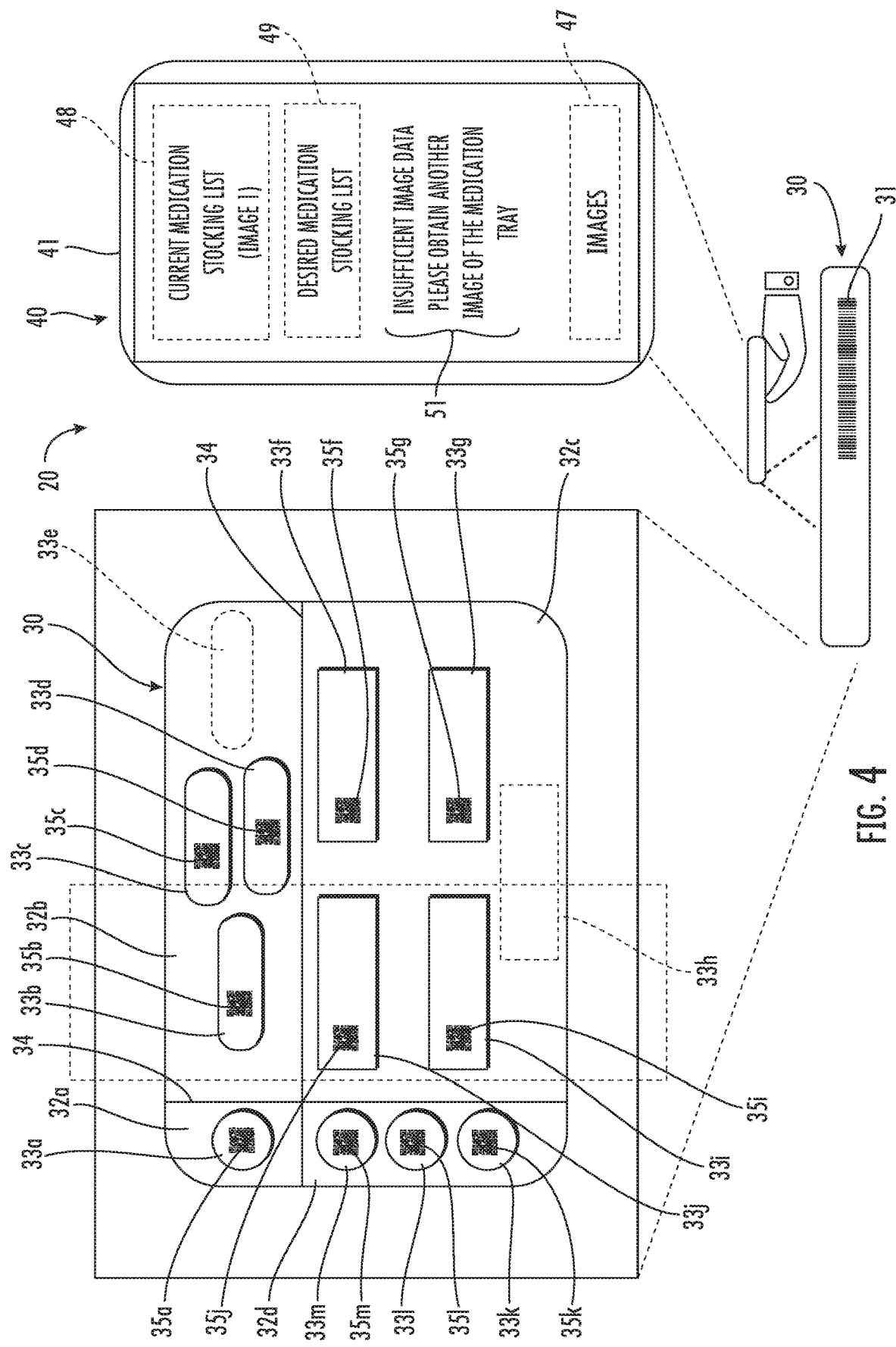
FIG. 4 is a schematic diagram of a medication inventory system in accordance with an embodiment.

Referring now additionally to the flowchart 60 in FIG. 3, beginning at Block 62, operations of the mobile wireless communications device 40 of the medication inventory system 20 will now be described. While operations of the mobile wireless communications device 40 are described, it will be appreciated by those skilled in the art that the controller 45 and an associated memory 46 cooperate to perform the operations.

At Block 64, the mobile wireless communications device 40 obtains images 47 of the medication tray 30. At Block 66, the mobile wireless communications device 40 generates a current medication stocking list 48 of the medication tray from the images 47.

The mobile wireless communications device 40 determines a desired medication stocking list 49 of the medication tray 30 based upon the tray identifier 31 (Block 68). More particularly, the mobile wireless communications device 40 may obtain the desired medication stocking list 49 from a remote computer or database based upon the tray identifier 31. In other words, the tray identifier 31 may be used as an index to retrieve or obtain the desired medication stocking list 49.

The mobile wireless communications device 40, at Block 70, determines one or more missing medications 33a-33n based upon the current medication stocking list 48 and the desired medication stocking list 49. More particularly, if a medication 33a-33n that is part of the desired medication stocking list 49 is determined to not be in the current medication stocking list 48 (i.e., a medication was not found in the images 47), a notification 51 may be generated and displayed on the display 43 of the mobile wireless communications device 40. The controller 45 may use image recognition techniques, for example, for identifying the medication identifiers 35a-35n, to determine missing medications. Operations end at Block 78.

Figure 8:
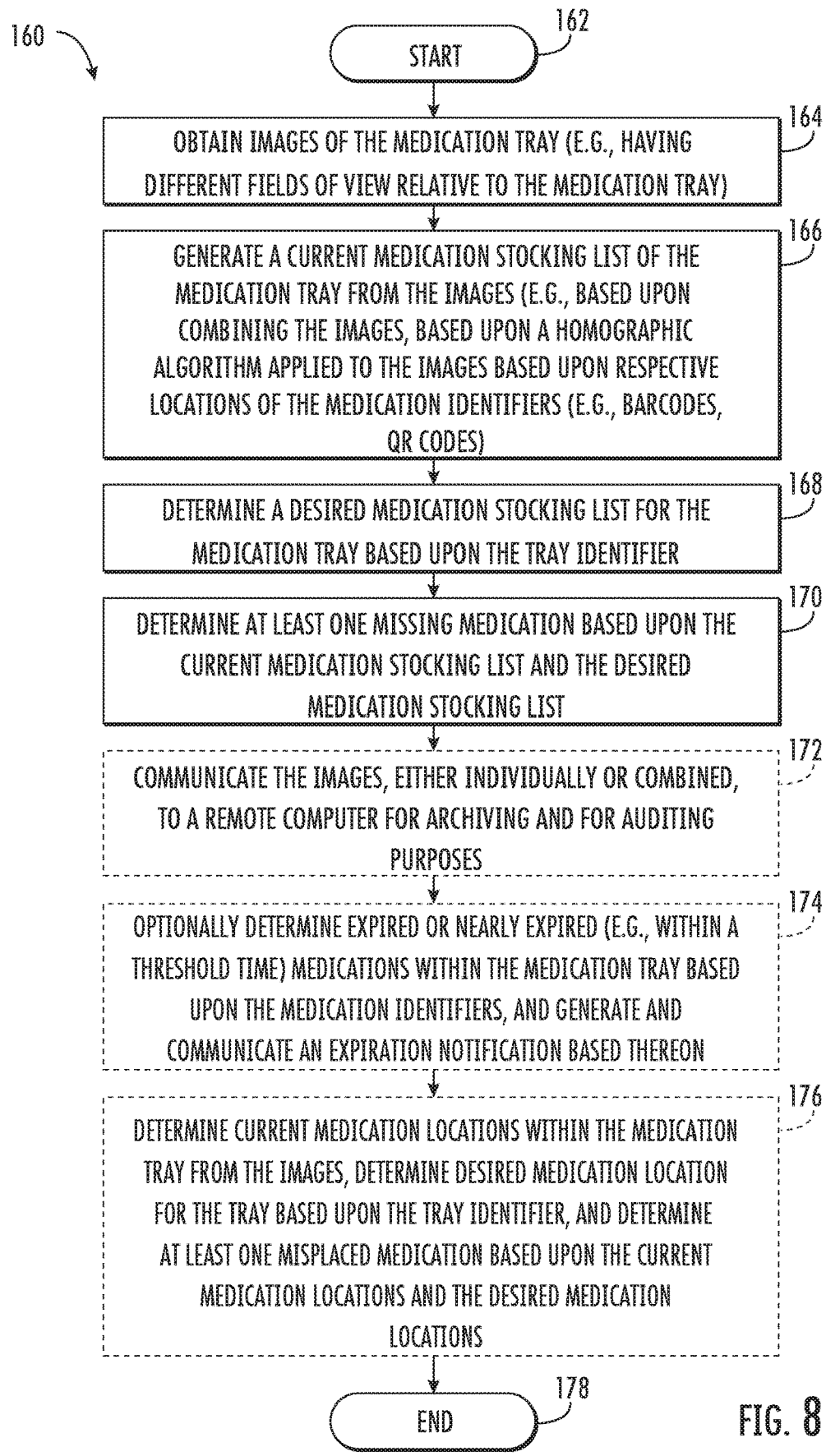
FIG. 8 is a flow diagram illustrating operation of the mobile wireless communications device of FIG. 4.

Referring now to FIGS. 4-7, and the flowchart 160 in FIG. 8, beginning at Block 162 more detailed operations of the mobile wireless communications device 40 with respect to the medication inventory system 20 will now be described. At Block 164, the mobile wireless communications device 40 obtains images 47 of the medication tray 30. The images 47 may include images having different fields of view relative to the medication tray 30. In other words, a given user may capture, via the camera 44, images of the medication tray 30. The images 47 may partially capture the medication tray 30. As will be appreciated by those skilled in the art, to obtain a high enough resolution to read both the tray and medication identifiers 31, 35, it may be desirable to position the mobile wireless communications device 40 including the camera 44 relatively close to the medication tray 30. As a result, a given image 47 may include only a portion of the medication tray 30 and thus not all medications 33a-33n would be in the field of view.

Figure 5:
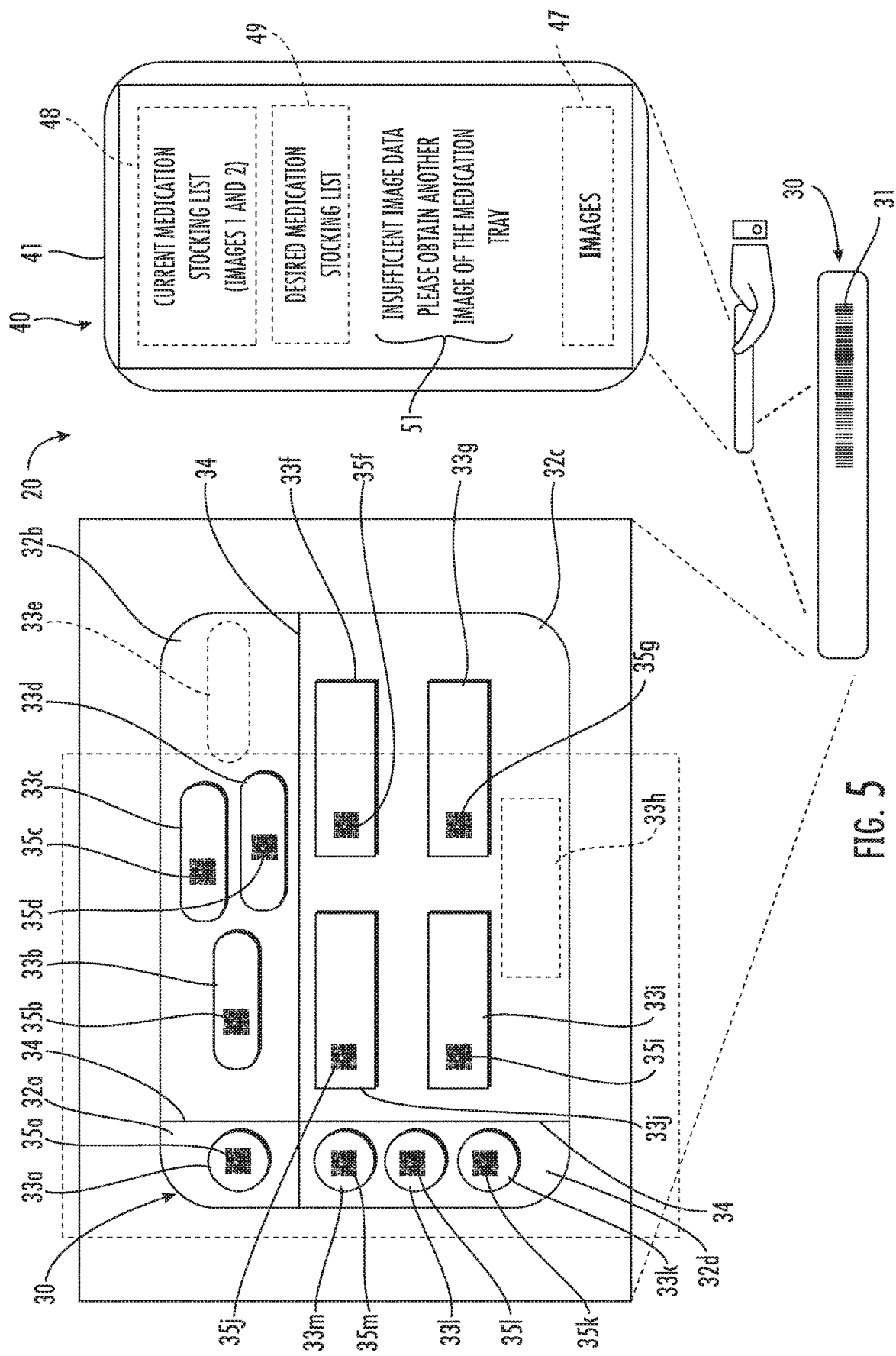
FIG. 5 is another schematic diagram of the medication inventory system in accordance with the embodiment of FIG. 4
Figure 6:
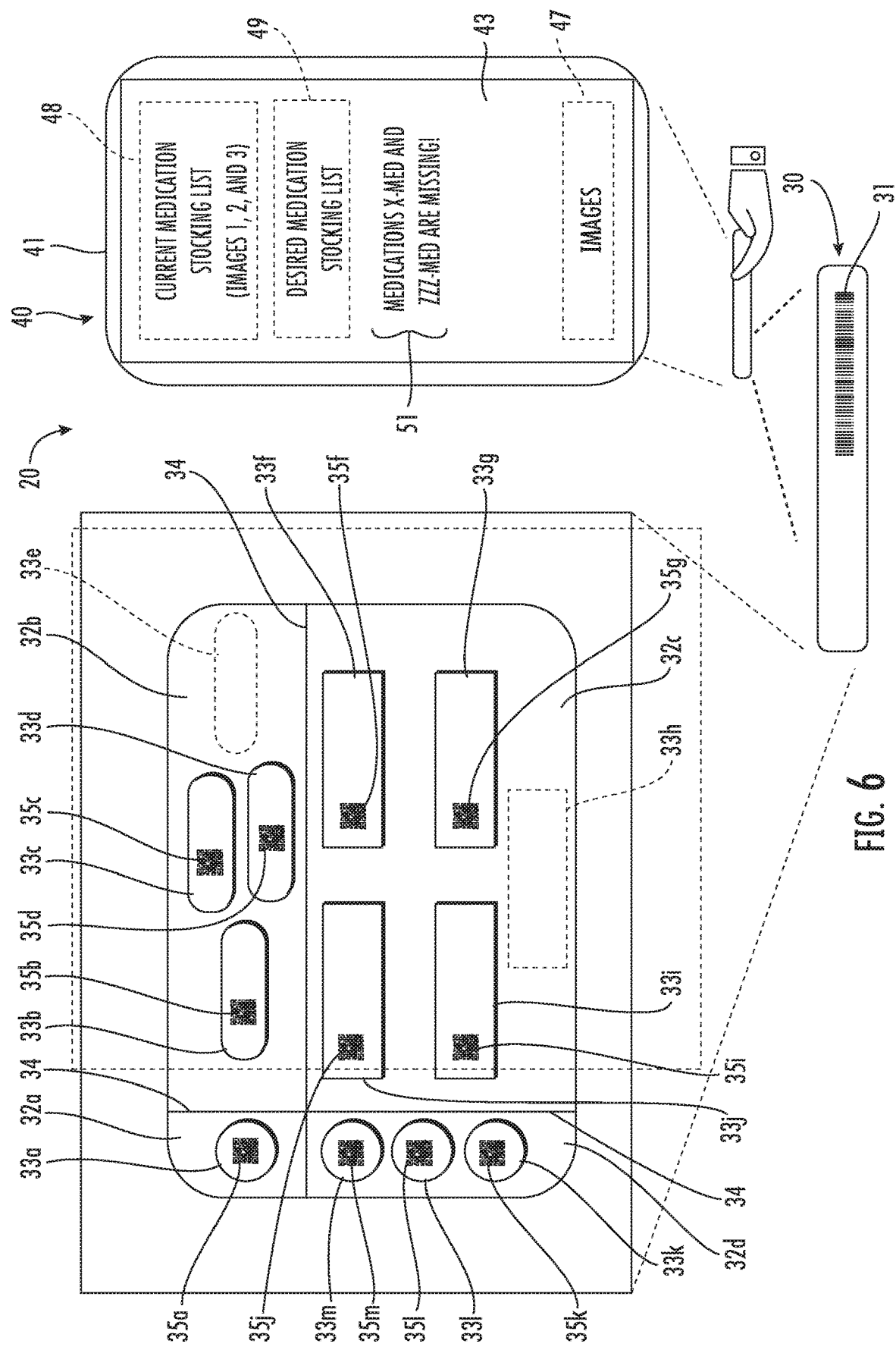
FIG. 6 is another schematic diagram of the medication inventory system in accordance with the embodiment of FIG. 4.
Figure 7:
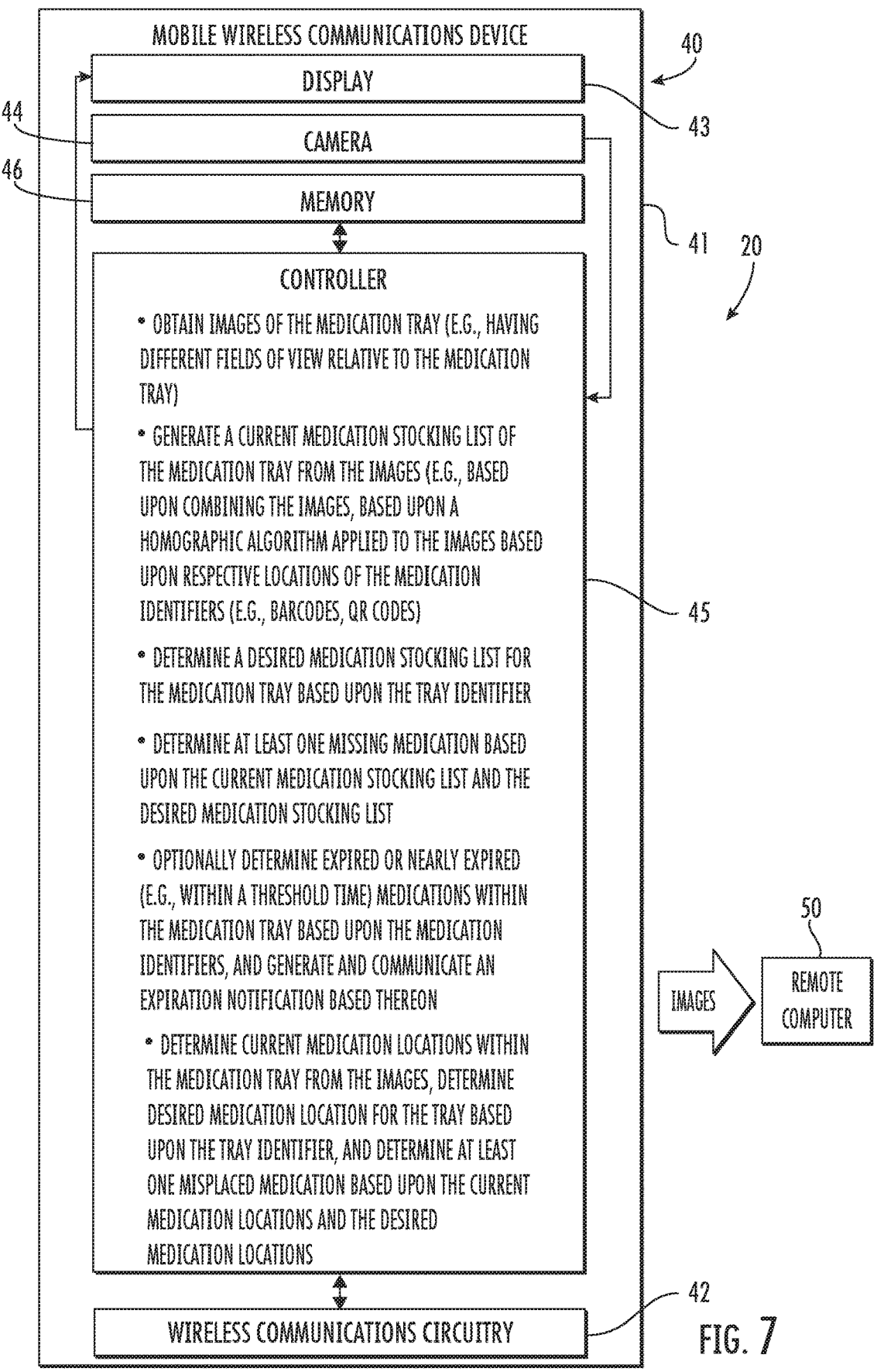
FIG. 7 is a schematic block diagram of the medication inventory system of FIG. 4.
Figure 9:
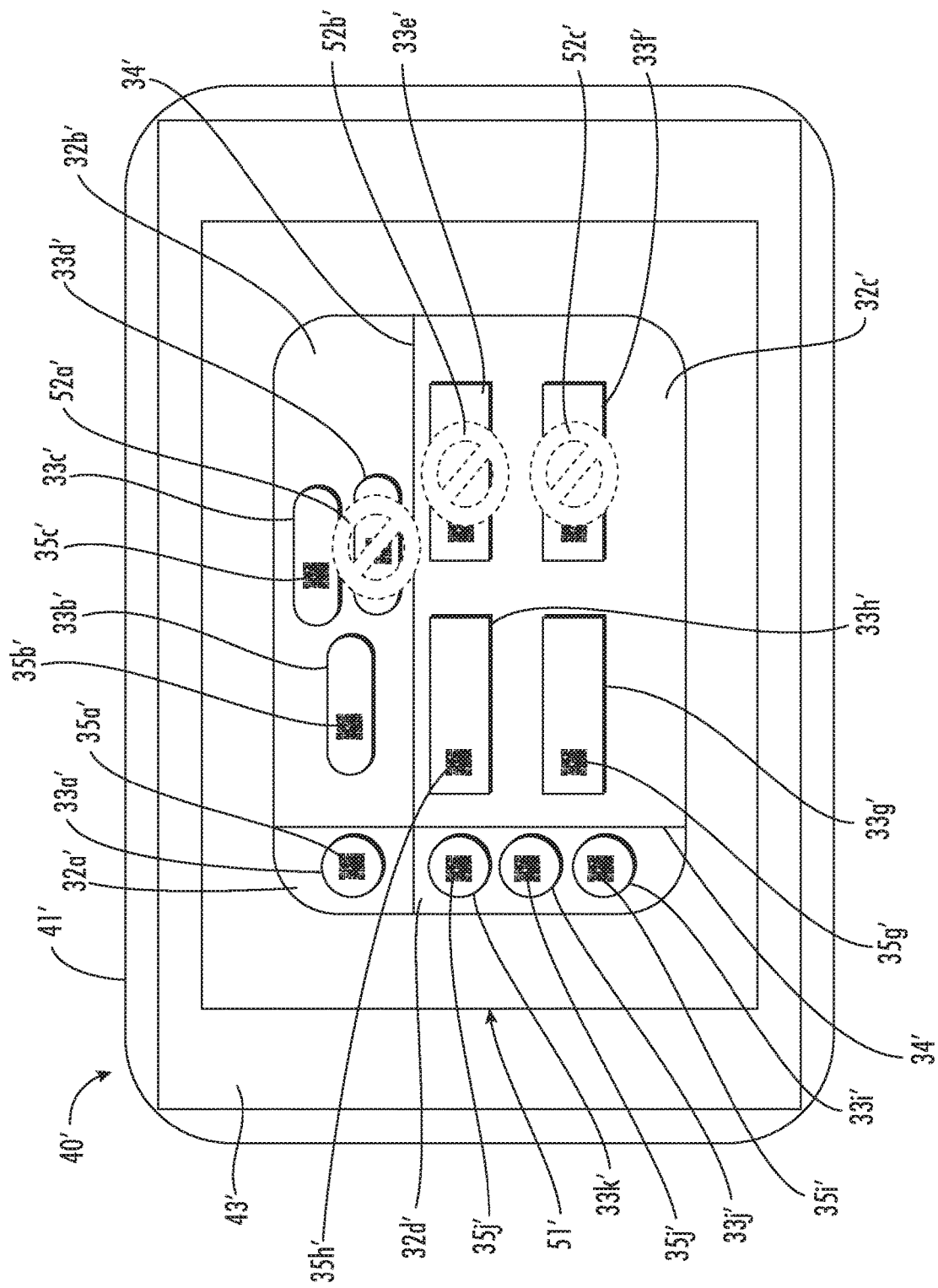
FIG. 9 is a schematic diagram of a mobile wireless communications device in accordance with another embodiment.

Moreover, a relative orientation of the mobile wireless communications device 40 to the medication tray 30 may result in some medication identifiers 35a-35n not being able to be read or decoded. Thus, the mobile wireless communications device 40 may generate a notification 51 as to whether a sufficient number of images has been obtained (FIGS. 5-6). Referring briefly to FIG. 9, in another embodiment, the notification 51' may be in the form of an image of the medication tray 30' on the display 43' of the mobile wireless communications device 40' and include indicia 52a'-52c', which may be color-coded, adjacent respective medications 33d'-33f' for which medication identifiers 35d'-35f' were unable to be identified or decoded.

At Block 166, the mobile wireless communications device 40 generates a current medication stocking list 48 of the medication tray 30 from the images 47. More particularly, the mobile wireless communications device 40 generates the current medication stocking list 48 based upon combining the images 47. For example, the mobile wireless communications device 40 may generate the current medication stocking list 48 based upon a homographic algorithm applied to the images 47, which may be based upon respective locations of the medication identifiers 35a-35n. An exemplary homographic algorithm, contrary to conventional homographic algorithms, does not use feature extraction or k-nearest-neighbor matching to provide the feature matches, but uses the individually identifiable identifiers (e.g., barcodes) already present in the process to provide feature matches, and as a result creates relatively consistent repeatable homographic processed images.

The mobile wireless communications device 40 determines a desired medication stocking list 49 of the medication tray 30 based upon the tray identifier 31 (Block 168), for example, using techniques along the lines described above. In some embodiments, desired medication stocking lists 49 for respective medication trays 30 may be stored in the memory 46 of the mobile wireless communications device 40.

The mobile wireless communications device 40, at Block 170, determines one or more missing medications 33e, 33h (e.g., that may have been used) based upon the current medication stocking list 48 and the desired medication stocking list 49. More particularly, if a medication that is part of the desired medication stocking list 49 is determined to not be in the current medication stocking list 48 (i.e., a medication 33e, 33h was not found in the combined images 47), a notification 51 may be generated and displayed on the display 43 of the mobile wireless communications device 40 and/or communicated. The notification 51 may be in the form of a list, for example, and/or an image of the medication tray with indicia (e.g. color-coded). The controller 45 may use image recognition techniques, for example, for identifying the medication identifiers 35a-35n, to determine missing medications. In some embodiments, the mobile wireless communications device 40 may determine that a medication is missing based upon there being less than a desired number (e.g., a threshold number) of medications in a given compartment.

In some embodiments, the mobile wireless communications device 40 may wirelessly communicate the images 47, either individually or combined, to a remote computer 50 for archiving and for auditing purposes (Block 172). The missing medications may also be wirelessly communicated to the remote computer 50. In some embodiments, the mobile wireless communications device 40 may generate and communicate an invoice for the missing medications. Alternatively or additionally, the mobile wireless communications device 40 may communicate the missing medications to a remote computer 50 for processing, for example, generation and communication of the invoices.

Figure 10:
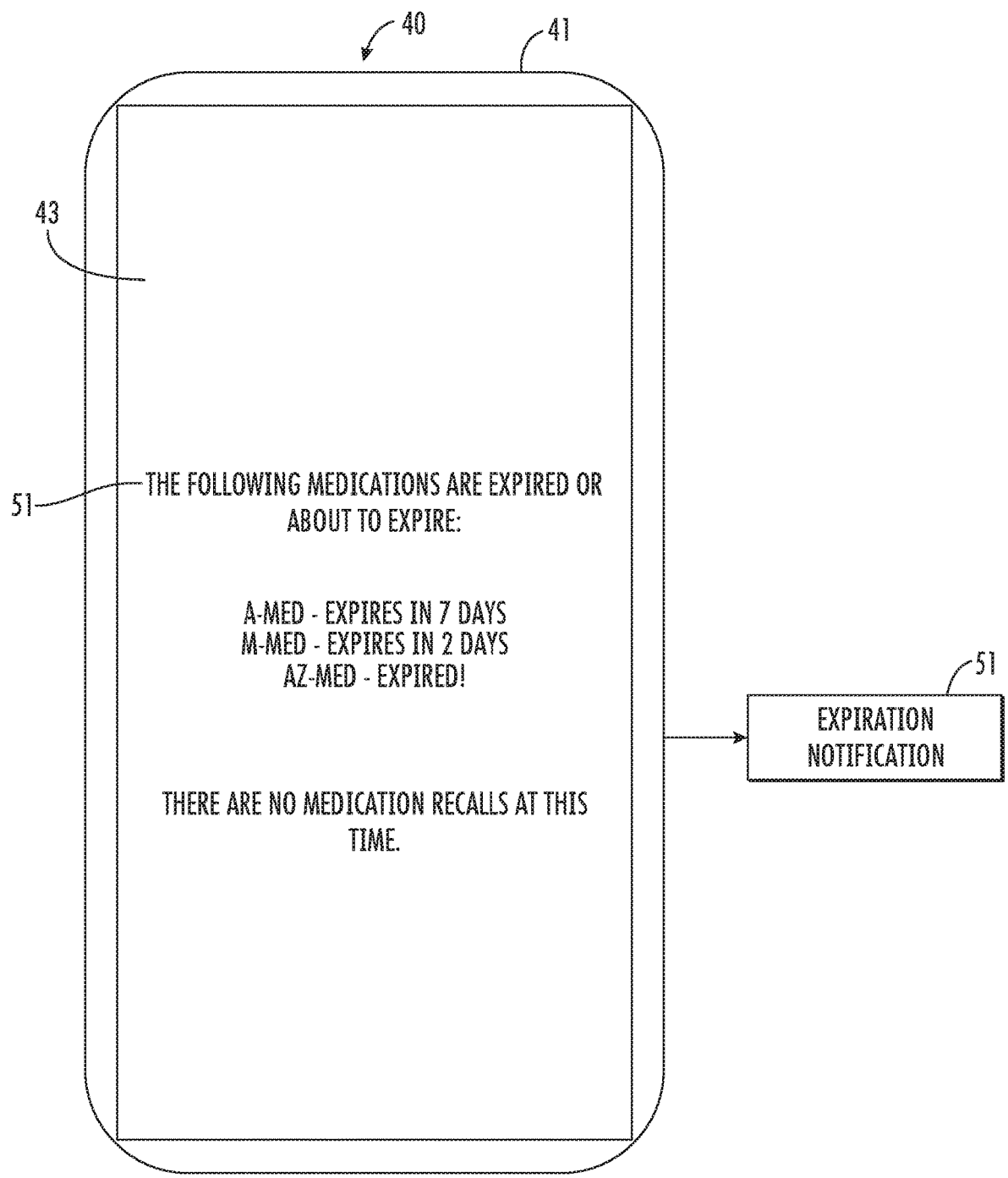
FIG. 10 is a schematic diagram of a mobile wireless communications device in accordance with an embodiment.

Referring now additionally to FIG. 10, the mobile wireless communications device 40 may also determine expired medications 33a-33n or nearly expired medications within the medication tray 30 based upon the medication identifiers 35a-35n (Block 174), for example, by comparing a lot number of the medication. The mobile wireless communications device 40 may generate an expiration notification 51 for display on the display 43 indicative of an expired medication or nearly expired medication (e.g., within a threshold time period from an actual expiration). The expiration notification 51 may also be communicated, for example, to a remote computer 50 or remote device. The mobile wireless communications device 40 may also determine recalled medications 33a-33n, for example, also based upon the lot number or other identifying information.

Figure 11:
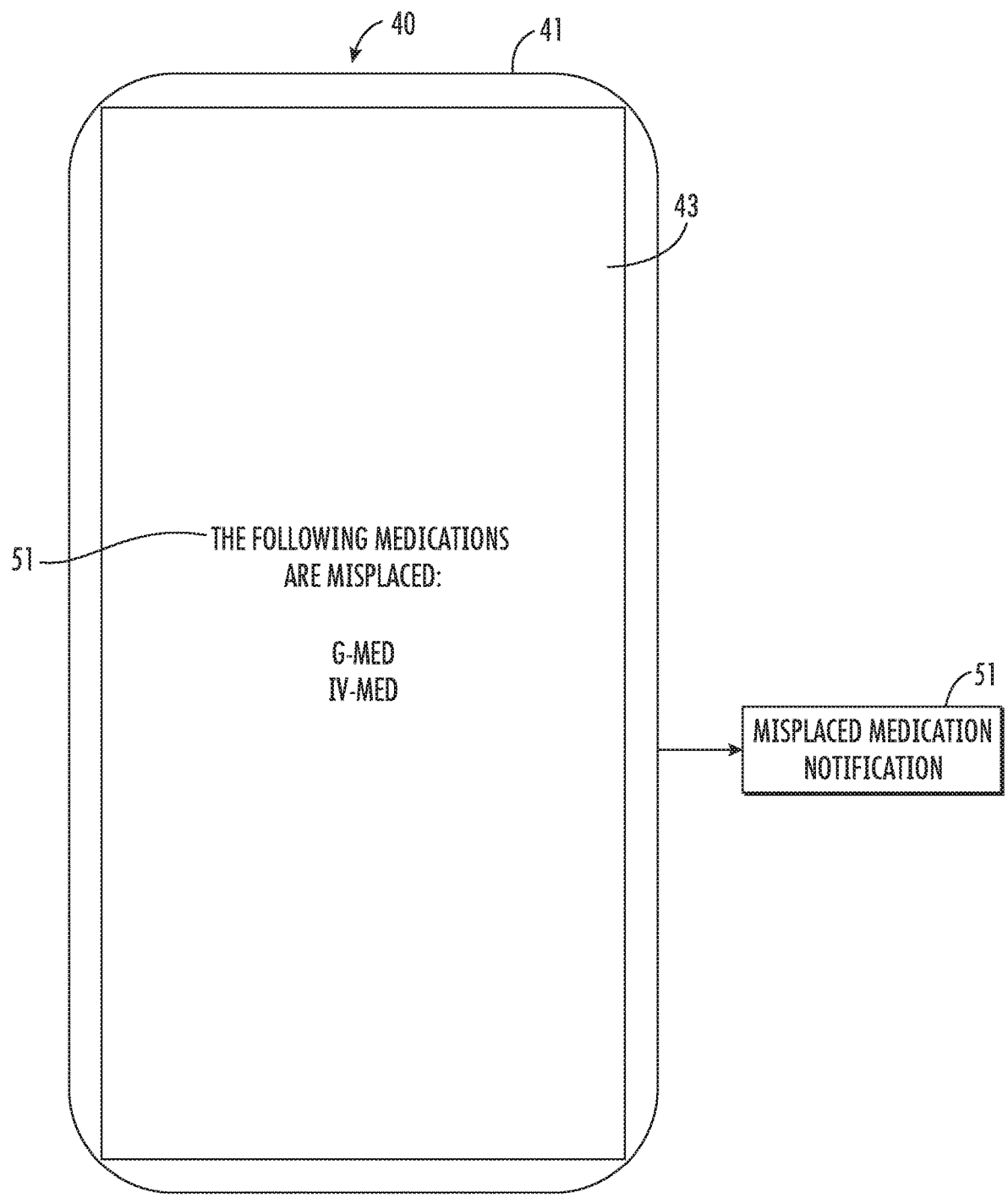
FIG. 11 is a schematic diagram of a mobile wireless communications device in accordance with an embodiment.

Referring now additionally to FIG. 11, the mobile wireless communications device 40 may determine one or more misplaced medications 33a-33n based upon current medication locations and desired medication locations (Block 176). More particularly, the mobile wireless communications device 40 may determine current medication locations within the medication tray 30 from the images 47 (e.g., based upon the medication identifiers 35a-35n) and determine desired medication locations for the tray based upon the tray identifier so that the misplaced medications are determined based upon the current medication locations and the desired medication locations. The mobile wireless communications device 40 may generate a misplaced medication notification 51 for display on the display 43 indicative of a misplaced medication (e.g., not in a correct compartment 32a-32n). The misplaced medication notification 51 may also be communicated, for example, to a remote computer 50 or remote device. In some embodiments, the medication tray 30 may be displayed on the display 43 of the mobile wireless communications device 40 along with the medications and indicia to indicate that one or more medications are misplaced. Operations end at Block 178.

As will be appreciated by those skilled in the art, the medication inventory system 20 may be particularly beneficial for ensuring hospital pharmaceutical trays are refilled efficiently and correctly using any of a variety of handheld device, for example. The medication inventory system 20 may integrate with current pharmacy safety/workflow and tracking technology, and provides pharmacy safety/workflow and tracking technology in a mobile or handheld form factor, thus supporting bring-your-own-device functionality.

Further details of medication trays and related processing of medications therein is described in U.S. patent application Ser. Nos. 16/448,493, 16/395,343, and 16/395,353, the entire contents of all of which is hereby incorporated by reference.

A method aspect is directed to a method of processing medication inventory in a medication inventory system 20 that includes a medication tray 30 including a plurality of compartments 32a-32n for storing respective medications 33a-33n with each medication having a respective medication identifier 35a-35n associated therewith. The medication tray 30 has a tray identifier 31 associated therewith. The method includes using a mobile wireless communications device 40 to obtain a plurality of images 47 of the medication tray 30 and generate a current medication stocking list 48 of the medication tray from the plurality of images. The method also includes using the mobile wireless communications device 40 to determine the desired medication stocking list 49 for the medication tray 30 based upon the medication tray identifier 31 and determine at least one missing medication 33a-33n based upon the current medication stocking list 48 and the desired medication stocking list.

A computer readable medium aspect is directed to a non-transitory computer readable medium for a medication inventory system 20 that includes a medication tray 30 including a plurality of compartments 32a-32n for storing respective medications 33a-33n with each medication having a respective medication identifier 35a-35n associated therewith. The medication tray 30 has a tray identifier 31 associated therewith, the non-transitory computer readable medium includes computer executable instructions that when executed by a controller 45 of a mobile wireless communications device 40 cause the controller to perform operations. The operations include obtaining a plurality of images 47 of the medication tray 30 and generating a current medication stocking list 48 of the medication tray from the plurality of images. The operations also include determining a desired medication stocking list 49 for the medication tray 30 based upon the tray identifier 31, and determining at least one missing medication 33a-33n based upon the current medication stocking list 48 and the desired medication stocking list.

While several embodiments have been described herein, it should be appreciated by those skilled in the art that any element or elements from one or more embodiments may be used with any other element or elements from any other embodiment or embodiments. Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A medication inventory system comprising:
    a medication tray comprising a plurality of compartments for storing respective medications with each medication having a respective medication identifier associated therewith, the medication tray having a tray identifier associated therewith; and
    a mobile wireless communications device configured to
        obtain a plurality of images of the medication tray,
        generate a current medication stocking list of the medication tray from the plurality of images,
        determine a desired medication stocking list for the medication tray based upon the tray identifier, and
        determine at least one missing medication based upon the current medication stocking list and the desired medication stocking list.

2. The medication inventory system of claim 1 wherein the mobile wireless communications device is configured to generate the current medication stocking list of the medication tray based upon combining the plurality of images.

3. The medication inventory system of claim 1 wherein the mobile wireless communications device is configured to generate the current medication stocking list of the medication tray based upon a homographic algorithm applied to the plurality of images.

4. The medication inventory system of claim 1 wherein the mobile wireless communications device is configured to generate the current medication stocking list of the medication tray based upon a homographic algorithm applied to the plurality of images based upon respective locations of the medication identifiers.

5. The medication inventory system of claim 1 wherein the mobile wireless communications device is configured to determine expired medications within the medication tray based upon the medication identifiers, and generate and communicate an expiration notification based thereon.

6. The medication inventory system of claim 1 wherein the mobile wireless communications device is configured to determine medications within the medication tray within a threshold time from expiration based upon the medication identifiers, and generate and communicate an expiration notification based thereon.

7. The medication inventory system of claim 1 wherein the plurality of images comprises a plurality of images having different fields of view relative to the medication tray.

8. The medication inventory system of claim 1 wherein the mobile wireless communications device is configured to:
    determine current medication locations within the medication tray from the plurality of images,
    determine desired medication locations for the tray based upon the tray identifier, and
    determine at least one misplaced medication based upon the current medication locations and the desired medication locations.

9. The medication inventory system of claim 1 wherein the mobile wireless communications device is configured to communicate the plurality of images to a remote computer for storage thereon.

10. The medication inventory system of claim 1 wherein the mobile wireless communications device comprises a housing and wireless communications circuitry carried by the housing.

11. The medication inventory system of claim 1 wherein the medication identifiers comprise barcodes.

12. The medication inventory system of claim 1 wherein the medication identifiers comprise quick-response (QR) codes.

13. A mobile wireless communications device for a medication inventory system comprising a medication tray comprising a plurality of compartments for storing respective medications with each medication having a respective medication identifier associated therewith, the medication tray having a tray identifier associated therewith, the mobile wireless communications device comprising:
  a controller and an associated memory configured to
    obtain a plurality of images of the medication tray,
    generate a current medication stocking list of the medication tray from the plurality of images,
    determine a desired medication stocking list for the medication tray based upon the tray identifier, and
    determine at least one missing medication based upon the current medication stocking list and the desired medication stocking list.

14. The mobile wireless communications device of claim 13 wherein the controller is configured to generate the current medication stocking list of the medication tray based upon combining the plurality of images.

15. The mobile wireless communications device of claim 13 wherein the controller is configured to generate the current medication stocking list of the medication tray based upon a homographic algorithm applied to the plurality of images.

16. The mobile wireless communications device of claim 13 wherein the controller is configured to generate the current medication stocking list of the medication tray based upon a homographic algorithm applied to the plurality of images based upon respective locations of the medication identifiers.

17. The mobile wireless communications device of claim 13 wherein the controller is configured to determine expired medications within the medication tray based upon the medication identifiers, and generate and communicate an expiration notification based thereon.

18. A method of processing medication inventory in a medication inventory system comprising a medication tray comprising a plurality of compartments for storing respective medications with each medication having a respective medication identifier associated therewith, the medication tray having a tray identifier associated therewith, the method comprising:
  using a mobile wireless communications device to
    obtain a plurality of images of the medication tray,
    generate a current medication stocking list of the medication tray from the plurality of images,
    determine a desired medication stocking list for the medication tray based upon the tray identifier, and
    determine at least one missing medication based upon the current medication stocking list and the desired medication stocking list.

19. The method of claim 18 wherein using the mobile wireless communications device comprises using the mobile wireless communications device to generate the current medication stocking list of the medication tray based upon combining the plurality of images.

20. The method of claim 18 wherein using the mobile wireless communications device comprises using the mobile wireless communications device to generate the current medication stocking list of the medication tray based upon a homographic algorithm applied to the plurality of images.

21. The method of claim 18 wherein using the mobile wireless communications device comprises using the mobile wireless communications device to generate the current medication stocking list of the medication tray based upon a homographic algorithm applied to the plurality of images based upon respective locations of the medication identifiers.

22. The method of claim 18 wherein using the mobile wireless communications device comprises using the mobile wireless communications device to determine expired medications within the medication tray based upon the medication identifiers, and generate and communicate an expiration notification based thereon.

23. A non-transitory computer readable medium for a medication inventory system comprising a medication tray comprising a plurality of compartments for storing respective medications with each medication having a respective medication identifier associated therewith, the medication tray having a tray identifier associated therewith, the non-transitory computer readable medium comprising computer executable instructions that when executed by a controller of a mobile wireless communications device cause the controller to perform operations comprising:
  obtaining a plurality of images of the medication tray;
  generating a current medication stocking list of the medication tray from the plurality of images;
  determining a desired medication stocking list for the medication tray based upon the tray identifier; and
  determining at least one missing medication based upon the current medication stocking list and the desired medication stocking list.

24. The non-transitory computer readable medium of claim 23 wherein the operations comprise generating the current medication stocking list of the medication tray based upon combining the plurality of images.

25. The non-transitory computer readable medium of claim 23 wherein the operations comprise generating the current medication stocking list of the medication tray based upon a homographic algorithm applied to the plurality of images.

26. The non-transitory computer readable medium of claim 23 wherein the operations comprise generating the current medication stocking list of the medication tray based upon a homographic algorithm applied to the plurality of images based upon respective locations of the medication identifiers.

27. The non-transitory computer readable medium of claim 23 wherein the operations comprise determining expired medications within the medication tray based upon the medication identifiers, and generate and communicate an expiration notification based thereon.

* * * * *